United States Patent
Fischer

(10) Patent No.: US 10,448,644 B2
(45) Date of Patent: Oct. 22, 2019

(54) FUNGICIDE COMPOSITION FOR NATURAL FIBERS AND NATURAL FIBER COMPONENTS

(71) Applicant: Lisa Draexlmaier Gmbh, Vilsbiburg (DE)

(72) Inventor: Wolfgang Fischer, Dorfen (DE)

(73) Assignee: Lisa Draexlmaier GmbH, Vilsbiburg (DE)

( * ) Notice: Subject to any disclaimer, the term of this patent is extended or adjusted under 35 U.S.C. 154(b) by 1051 days.

(21) Appl. No.: 14/876,756

(22) Filed: Oct. 6, 2015

(65) Prior Publication Data

US 2016/0095319 A1 Apr. 7, 2016

(30) Foreign Application Priority Data

Oct. 7, 2014 (DE) .................. 10 2014 114 539

(51) Int. Cl.

| | | |
|---|---|---|
| *D06M 11/57* | (2006.01) | |
| *A01N 59/06* | (2006.01) | |
| *D06M 16/00* | (2006.01) | |
| *D06M 101/02* | (2006.01) | |
| *D06M 101/06* | (2006.01) | |

(52) U.S. Cl.
CPC ............ *A01N 59/06* (2013.01); *D06M 11/57* (2013.01); *D06M 16/00* (2013.01); *D06M 2101/02* (2013.01); *D06M 2101/06* (2013.01)

(58) Field of Classification Search
CPC ...... A01N 59/06; D06M 11/57; D06M 16/00; D06M 2101/02; D06M 2101/06
See application file for complete search history.

(56) References Cited

U.S. PATENT DOCUMENTS

| | | | |
|---|---|---|---|
| 1,634,794 A | 7/1927 | Minaeff et al. | |
| 2009/0220560 A1* | 9/2009 | Wan ..................... | A61L 15/46 424/409 |
| 2010/0055142 A1 | 3/2010 | Heagle et al. | |
| 2010/0272690 A1* | 10/2010 | Gandhi ................. | A01N 31/02 424/93.5 |

FOREIGN PATENT DOCUMENTS

| | | |
|---|---|---|
| CN | 101812773 A | 8/2010 |
| DE | 69220689 T2 | 12/1997 |
| EP | 2 031 011 A1 | 5/2007 |
| JP | S 60146809 A | 8/1985 |

* cited by examiner

*Primary Examiner* — Christina A Johnson
*Assistant Examiner* — Xue H Liu
(74) *Attorney, Agent, or Firm* — Finnegan, Henderson, Farabow, Garrett & Dunner LLP

(57) ABSTRACT

A method for producing a natural fiber part may comprise applying an aqueous solution of an inorganic aluminum salt to the natural fiber part and drying the natural fiber part applied with the aqueous solution. The aqueous solution may contain the aluminum salt in a concentration of 2 to 40% by weight. The aluminum salt may include an alum compound. At least one of an inorganic thickening agent or an inorganic stabilizing agent may be added to the aqueous solution.

5 Claims, 1 Drawing Sheet

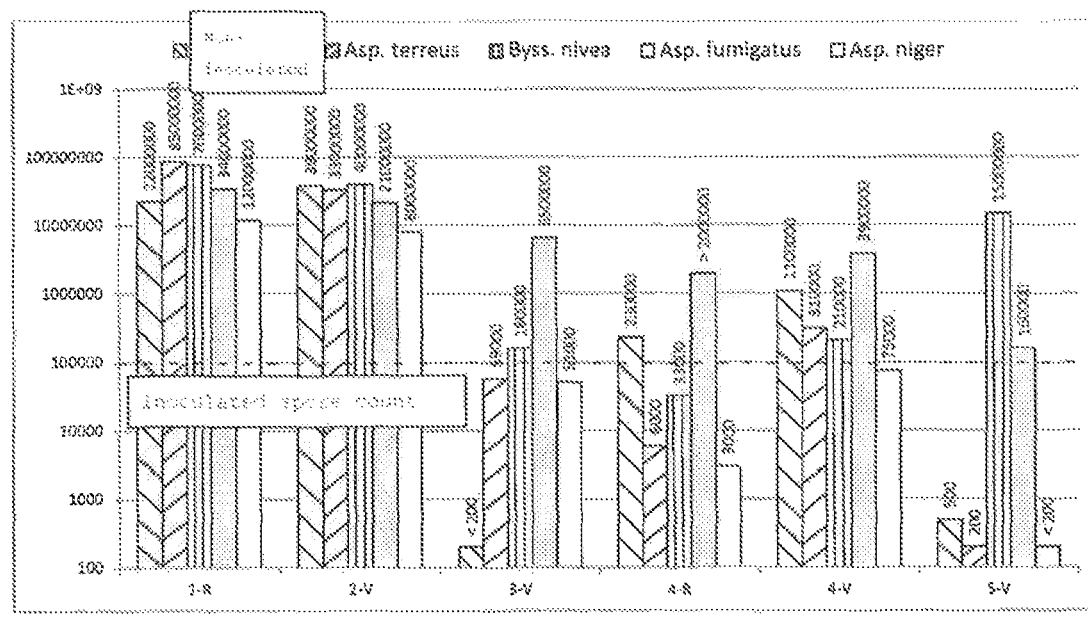

FUNGICIDE COMPOSITION FOR NATURAL FIBERS AND NATURAL FIBER COMPONENTS

CROSS-REFERENCE TO RELATED APPLICATION

This application is based upon and claims the benefit of prior German Application No. 10 2014 114 539.9, filed on Oct. 7, 2014, the entire contents of which are incorporated herein by reference.

TECHNICAL FIELD

The present disclosure relates to a fungicide-containing natural fiber shaped part, to a method for the production thereof, and to the use of at least one non-toxic inorganic aluminum salt.

BACKGROUND OF THE DISCLOSURE

Automakers are increasingly relying on the mixed use of chemical and natural fibers in automobiles. In addition to the sustainability aspect and the use of renewable resources associated therewith, manufacturers may seek to save weight by using alternative materials and material combinations.

In addition, natural fibers such as sisal, coconut or hemp are no longer used only in non-visible functional components automobiles, and may also be used in a visible area, such as in the vehicle interior. The requirements of these materials are often very high. Even under constantly changing temperature and moisture conditions, microorganisms should not be allowed to settle. When microorganisms are allowed to settle, undesirable visual effects, such as mildew stains, may occur. Further, unpleasant odors may be generated in the vehicle interior. While resistance to such undesirable visual effects and odors must be ensured over the life of the vehicle, the focus after decommissioning of the vehicle, in contrast, is placed on swift and substantially residue-free decomposition of the interior fittings and attachment parts in the spirit of protecting the environment.

Natural fibers and wood may be quickly subject to the growth of mold due to moisture and heat, which is undesirable for the surface appearance and for health reasons. The risk of mold growth may be high in parts made of compressed natural fiber-reinforced polymer composites.

A large variety of corresponding fungicides exist; however they may be applied and used only conditionally, based on the Ordinance on Hazardous Substances, and additionally may change the mechanical and visual properties of the parts produced therefrom, which are used in the automobile interior.

The group of organic active fungicidal agents has a heterogeneous composition and can be difficult to manage. For example, thiabendazole, an active agent from the group of benzimidazoles, may be used as a systemic fungicide having protective and curative activity for natural fibers. While the toxicity of thiabendazole is low according to the German Federal Institute for Health Protection and Veterinary Medicine, the substance was found to have a carcinogenic effect in animal experiments.

SUMMARY

Embodiments of the present disclosure provide an environmentally compatible fungicidal composition that can be used to treat natural fibers or natural fiber components, and offers lasting protection from mold growth. Corresponding fungicide-containing natural fibers and/or a natural fiber shaped part may also be provided.

Inorganic aluminum salts meet the described requirements.

Embodiments of the present disclosure include a fungicide-containing natural fiber shaped part, a method for producing fungicide-containing natural fibers, a natural fiber shaped part, and use of the foregoing parts.

The present disclosure provides that the natural fibers and/or the natural fiber shaped part may comprise one or more inorganic aluminum salts for combating and preventing mold growth.

The majority of inorganic aluminum salts, such as aluminum potassium sulfate dodecahydrate, for example, are not classified hazardous according to legislation of the European Union (EU). Further, according to Regulation (EC) 1272/2008, the majority of inorganic aluminum salts do not constitute hazardous substances, contrary to conventional organic active fungicidal agents, which may be used as systemic fungicides having protective and curative activity.

Aluminum potassium sulfate dodecahydrate has comparable fungicidal properties. Aluminum potassium sulfate dodecahydrate may be used in foodstuffs as a firming agent or stabilizer. In the EU, the use thereof as a food additive by the designation E 522 is restricted to egg white as well as glazed, candied or crystallized fruits and vegetables. In addition, potash alum may be used under the trade name LMA against fire blight. Even today, it may be used as an "alum block" to stop bleeding or in modeling clays for children's toys. Due to the odor-inhibiting effect, it may also be contained in some deodorants.

In this way, a fungicide that may be inexpensive and may not pose a health hazard is provided for natural fibers and/or natural fiber shaped parts, which can already be used during the production of the shaped part in an application method.

The aluminum salt may be selected from the group of alum compounds ($M^{I}M^{III}(SO_4)_2 \cdot 12H_2O$) and/or a mixture thereof. Alum may be used in a variety of ways, wherein almost exclusively only the aluminum sulfate may take effect.

Alum used to be referred to only as the crystallized hydrated double sulfate salt of potassium and aluminum (potassium aluminum sulfate). The corresponding ammonium aluminum salt may also be referred to in this way, while the term alums may also apply to all sulfuric double bonds having a like chemical constitution, wherein the metal taking the place of potassium or aluminum then precedes the designation, such as chrome alum for the double sulfate salt of potassium and chrome, for example.

Aluminum salt may be applied to the natural fibers and/or the natural fiber shaped part as an aqueous alum solution ($KAl(SO_4)_2 \cdot 12H_2O$, potassium aluminum sulfate dodecahydrate) in a concentration of, for example, 2 to 40% by weight. Potassium aluminum sulfate dodecahydrate can be a particularly efficient fungicide for natural fibers and/or natural fiber shaped parts and can be applied already during the production of the shaped part from an aqueous solution in a simple application process. In addition, it is not considered to pose a health hazard and is available as an inexpensive raw material.

Inorganic thickening and/or stabilizing agents may be added to the aluminum salt or the aluminum salts. These additives can improve the adhesion and homogeneous distribution of the fungicidal aluminum salt in or on the natural fibers and/or the natural fiber shaped parts. Polymers can be used as stabilizing agents.

The natural fibers and/or the natural fiber component may comprise at least one coating, which may be based on the aforementioned salts, solutions and mixtures, produced by way of spraying, dusting, flow coating, dipping or brushing and the like. The coating may result from an application process from the solution after drying, for example during production of the shaped part.

A method according the present disclosure for producing fungicide-containing natural fibers and/or a natural fiber molded part may comprise the treatment of the same by way of spraying, dusting, flow coating, dipping or brushing, for example, followed by drying. The described treatment methods may allow for a substantially homogeneous distribution of the dissolved active agent in the shaped part or the natural fiber. The treatment of the natural fibers may be carried out prior to compressing the same to form a natural fiber shaped part. In this way, a substantially homogeneous distribution of the active agents in the shaped part can be ensured.

The step of drying the natural fibers and/or the natural fiber shaped part may be carried out prior to compressing the same in a temperature range of 20 to 90° C., for example. During the step of drying, the substantially homogeneous distribution of the active fungicidal agent may be followed by fixing the same in or on the natural fibers and/or the natural fiber shaped part.

A use according to the present disclosure may relate to at least one non-toxic, inorganic aluminum salt for combating and preventing mold growth on natural fibers and/or natural fiber shaped parts according to the above-mentioned embodiments.

An aqueous alum solution ($KAl(SO_4)_2 \cdot 12H_2O$, potassium aluminum sulfate dodecahydrate) in a concentration of 2 to 40% by weight, for example, may be used.

As an alternative or in addition, an aqueous aluminum sulfate solution ($Al(SO_4)_3$) in a concentration of 2 to 40% by weight, for example, may be used.

This concentration range can be particularly efficient and practical for natural fibers and/or natural fiber shaped parts with potassium aluminum sulfate dodecahydrate.

Inorganic thickening and/or stabilizing agents may be added to the aluminum salt.

BRIEF DESCRIPTION OF THE FIGURE

FIG. 1 shows an overview of viable count.

DETAILED DESCRIPTION

Embodiments of the present disclosure will be described in more detail hereafter based on several examples.

The examples hereafter in Table 1 show different passenger car door interior trims, which all have a polymer/natural fiber structure.

TABLE 1

| Analyzed natural fiber-containing components | |
|---|---|
| Material | Description |
| 1-R | Door trim containing no fungicide; Material PP-KE-PES (45-40-15); Inoculation: back |
| 2-V | Component packaged directly after production (no microbial contamination from the air); Inoculation: front |

TABLE 1-continued

| Analyzed natural fiber-containing components | |
|---|---|
| Material | Description |
| 3-V | Door trim containing thiabendazole; Inoculation: front |
| 4-R, 4-V | Climate layer containing thiabendazole; Inoculation: back and front |
| 5-V | Door trim containing 5% alum; Inoculation: front |

The analysis includes inoculated components containing no fungicide, components containing thiabendazole, and components treated with a 5% alum solution ($KAl(SO_4)_2 \cdot 12H_2O$, potassium aluminum sulfate dodecahydrate).

The components inoculated with test microorganisms were partially sterilized over-night prior to inoculation at 100° C. The inoculation with the respective test microorganisms was carried out on the front and/or back. The components were exposed to the test microorganisms over 14 days.

The respective test piece is suspended and coated with test microorganisms in different dilutions. The following fungus types were analyzed:
  Asp. terreus
  Byss. nivea
  Asp. Fumigatus
  Asp. Niger The culture media were incubated over at least 3 days at 30° C. The final evaluation and calculation of the "colony-forming units" (CFU) per test piece were carried out by way of microscopic-optical evaluation. The assessment scale is shown in Table 2.

TABLE 2

| Assessment scale | | |
|---|---|---|
| CFU/test piece | Non-inoculated test pieces | Inoculated test pieces |
| $<10^3$/pc. | fungicidally effective | fungicidally effective |
| $10^3$-$10^5$/pc. | Suspected microbial instability | |
| $10^5$/pc. | microbially unstable | fungistatically effective |
| $10^5$-$10^6$/pc. | | Suspected microbial instability |
| $>10^6$/pc. | | microbially unstable |

Table 3 hereafter shows the results of a visual rating after 14 days at 100% relative humidity and 30° C.:

TABLE 3

Results of a visual rating after 14 days at 100% relative humidity and 30° C.

| Test pieces | Non-inoculated | Asp. terreus | Byss. nivea | Asp. fumigatus | Asp. niger |
|---|---|---|---|---|---|
| 1-R | ++ | ++ | + | + | +++ |
| 2-V | + | ++ | +++ | + | +++ |
| 3-V | unr. | unr. | + | + | + |
| 4-R | unr. | + | + | unr. | + |
| 4-V | unr. | + | + | unr. | ++ |
| 5-V | unr. | unr. | +++ | unr. | unr. | unr.: unremarkable, no microbial surface growth visible
+: if minute traces of microbialgrowth are visible
++: if microbial growth on <5% of the inoculated surface is visible
+++: if microbial growth on >5% of the inoculated surface is visible Untreated test components developed dense mycelium with test microorganisms on the culture medium with easily usable nutrients. FIG. 1 shows an overview of viable count.

Materials were exposed for 14 days at 100% r.h. and 30° C.

Materials 1-R and 2-V containing no fungicide develop extremely pronounced mold growth.

Materials 3-V, 4-R and 4-V containing thiabendazole had considerably reduced contents of viable counts. The dosage is still low and can be increased. Some fungus types exhibited clearly inhibited growth. *Asp. fumigatus* was inhibited only insignificantly. The active agent is known to have wide ranges in effectiveness with respect to different fungus types. In sufficient concentration, the described aluminum salts exhibit a fungistatic effect.

Material 5-V containing alum was colonized only by *Byss. nivea*; the growth of the other three test microorganisms was impeded or largely inactivated.

The invention claimed is:

1. A method for producing a natural fiber part, the method consisting essentially of:
    applying an aqueous solution of an inorganic aluminum salt to the natural fiber part, the aqueous solution consisting essentially of the aluminum salt in a concentration of 2 to 40% by weight; and
    drying the natural fiber part applied with the aqueous solution in a temperature range of 30° C. to 90° C.,
    wherein the aluminum salt is an alum compound of the formula $M^{I}M^{III}(SO_4)_2 \cdot 12H_2O$ and/or a mixture thereof, and
    wherein at least one inorganic thickening agent, at least one inorganic stabilizing agent, or a mixture thereof is added to the aqueous solution.

2. The method according to claim 1, further comprising:
    compressing, after the aqueous solution is applied, the natural fiber part to form a natural fiber shaped part.

3. The method according to claim 2, wherein drying the natural fiber part is performed prior to compressing the natural fiber part.

4. The method according to claim 1, wherein the aluminum salt is configured to reduce mold growth.

5. The method according to claim 1, wherein the aqueous solution is an aqueous potassium aluminum sulfate dodecahydrate solution in a concentration of 2 to 40% by weight.

* * * * *

UNITED STATES PATENT AND TRADEMARK OFFICE
CERTIFICATE OF CORRECTION

PATENT NO.        : 10,448,644 B2
APPLICATION NO.   : 14/876756
DATED             : October 22, 2019
INVENTOR(S)       : Wolfgang Fischer Page 1 of 1

It is certified that error appears in the above-identified patent and that said Letters Patent is hereby corrected as shown below:

On the Title Page

Item (30), Line 1, "10 2014 114 539" should read -- 10 2014 114 539.9 --

Signed and Sealed this
Twenty-fourth Day of December, 2019

Andrei Iancu
*Director of the United States Patent and Trademark Office*